US005745595A

United States Patent [19]
Yamada et al.

[11] Patent Number: 5,745,595
[45] Date of Patent: Apr. 28, 1998

[54] SURFACE ANALYSIS INSTRUMENT AND METHOD OF DISPLAYING IMAGES USING INFORMATION OBTAINED BY SURFACE ANALYSIS

[75] Inventors: Hiroyuki Yamada; Masaki Saito; Masayuki Ohtsuki, all of Tokyo, Japan

[73] Assignee: JEOL Ltd., Tokyo, Japan

[21] Appl. No.: 628,245

[22] Filed: Apr. 4, 1996

[30] Foreign Application Priority Data

Apr. 11, 1995 [JP] Japan ................... 7-085294

[51] Int. Cl.[6] ................... G06K 9/00
[52] U.S. Cl. ................... 382/170; 382/108; 382/171; 382/282
[58] Field of Search ................... 382/168, 169, 382/170, 171, 172, 180, 164, 108, 109, 282; 348/32, 34; 395/131; 345/35, 36, 37, 38, 133, 140; 250/310

[56] References Cited

U.S. PATENT DOCUMENTS 4,847,786  7/1989  Wang et al. ................... 382/171
4,857,731  8/1989  Tagata ................... 250/310
5,332,968  7/1994  Brown ................... 324/309

OTHER PUBLICATIONS

"Phase Analysis by Computer Processing in EPMA (Electron Probe Microanalyzer)", Hideyuki Takahashi, Masayuki Otsuki and Toyohiko Okumura, JEOL News, vol. 31E, No. 1 28 (1994), pp. 28–32.

Primary Examiner—Leo Boudreau
Assistant Examiner—Phuoc Tran
Attorney, Agent, or Firm—Webb Ziesenheim Bruening Logsdon Orkin & Hanson, P.C.

[57] ABSTRACT

A surface analysis instrument such as an electron probe microanalyzer. The instrument makes surface analyses of different regions on a sample and displays images of the regions according to the obtained information at different positions on the viewing screen of a display unit. The instrument creates a mixed histogram of the regions from the information about the regions. A level assortment is carried out according to the mixed histogram. Information about the level assortment is stored in a memory. Colors are assigned to images of the different regions according to the information about the level assortment. The images are displayed at different positions on the viewing screen.

12 Claims, 7 Drawing Sheets

SURFACE ANALYSIS INSTRUMENT AND METHOD OF DISPLAYING IMAGES USING INFORMATION OBTAINED BY SURFACE ANALYSIS

FIELD OF THE INVENTION

The present invention relates to a surface analysis instrument such as an electron probe microanalyzer (EPMA) and also to a method of displaying images using information obtained by surface analysis.

BACKGROUND OF THE INVENTION

An electron probe microanalyzer (EPMA) is an instrument for directing an electron beam to a sample, detecting characteristic X-rays emitted from the sample, and identifying elements which constitute the sample from the characteristic X-rays.

When a surface analysis is made with an electron probe microanalyzer (EPMA), either the electron beam or the sample stage is scanned so that the irradiated point (analyzed point) on the sample moves at appropriate intervals within a region to be analyzed. The intensity of the characteristic X-rays at each analyzed point is accepted as data about the two-dimensional distribution. That is, the data is obtained for performing a surface analysis. Based on this data about the two-dimensional distribution, a map representing the characteristic X-ray intensities arising from the analyzed region is represented as a color image. This color representation is described in further detail. For example, where the map of characteristic X-ray intensities is displayed in 16 colors, the range of intensities of the X-rays from the minimum value to the maximum value, i.e., dynamic range, is divided into 16 subranges. A different color is assigned to each individual subrange. When data indicating characteristic X-rays having an intensity is accepted, a color corresponding to the intensity is assigned to the subrange. As a result, a map of characteristic X-ray intensities is displayed as a color image on a display unit.

However, depending on the sample, the distribution of the intensities of characteristic X-rays may be concentrated in a narrow range. In this case, if the colors are assigned as described above, then the map presented on the display unit consists of very few colors, for example, one or two colors. This makes it impossible to make a detailed analysis or discussion based on the map. Accordingly, an electron probe microanalyzer is equipped with a multi-color display range modification function to permit the user to arbitrarily specify a multi-color display range within the dynamic range. By using this function, a more detailed map of characteristic X-ray intensities can be created even if the intensities of characteristic X-rays are concentrated in a narrow range.

In electron probe microanalysis, different small regions on a sample are subjected to surface analysis. A plurality of maps are presented on the same display unit based on obtained data about the different regions. The aforementioned multi-color display range modification function is applied to each different map. When one tries to compare the plural maps on the display unit of the prior art electron probe microanalyzer, the multi-color display range modification function is applied to each different map. It is necessary to establish this multi-color display range common to every map. Since this operation must be carried out for all the maps, the operation is time-consuming and complex.

SUMMARY OF THE INVENTION

It is an object of the present invention to provide a surface analysis instrument capable of creating maps which are easy to compare.

It is another object of the invention to provide a method of displaying images, using information obtained by surface analysis, in such a way that comparison of maps is facilitated.

A surface analysis instrument, according to the present invention, makes surface analyses of different regions on a sample and displays images of the different regions at different positions on a viewing screen based on the obtained information. This surface analysis instrument comprises a means for creating a mixed histogram of the plural regions from the information obtained by the surface analyses, a means for performing an assortment by level according to the mixed histogram, a storage means for storing data about the assortment, a means for assorting the images of the regions according to their levels based on information about the assortment by level from the mixed histogram, and a display means having the viewing screen on which the images are displayed at different positions.

Another surface analysis instrument according to the invention makes surface analyses of different regions on a sample and displays images of the different regions at different positions on a viewing screen based on the gathered information. This surface analysis instrument comprises a means for permitting a user to select one from the plural regions, a means for making a surface analysis of the selected region and producing information indicating results of the analysis, a means for creating a histogram of the region from the information, a means for performing an assortment by level according to the histogram, a storage means for storing data about the assortment, a means for assorting the images of the regions according to their levels based on information about the level assortment, and a display means having the viewing screen on which the images are displayed at different positions.

A method of displaying images using information gathered by surface analyses, according to the invention, performs surface analyses of different regions on a sample. Images of the regions are displayed at different positions on the viewing screen of a display unit. This method comprises the steps of: creating a mixed histogram of the regions from the information obtained by the surface analyses; performing an assortment by level according to the mixed histogram; and displaying images of the regions at different positions on the viewing screen according to information about the level assortment.

Another method of displaying images using information gathered by surface analyses, according to the invention, is intended to perform surface analyses of different regions on a sample. Images of the regions are displayed at different positions on a viewing screen. This method comprises the steps of: selecting one from the plural regions; making a surface analysis of the selected region; creating a histogram of the region according to information about the selected region; performing a level assortment according to the histogram; applying results of the level assortment to the information about the plural regions; and displaying images of the regions at different positions on the viewing screen.

BRIEF DESCRIPTION OF THE DRAWINGS

Further features and other objects and advantages of the invention will be apparent from the following detailed description made with reference to the drawings in which.

DETAILED DESCRIPTION OF THE INVENTION

Figure 1:
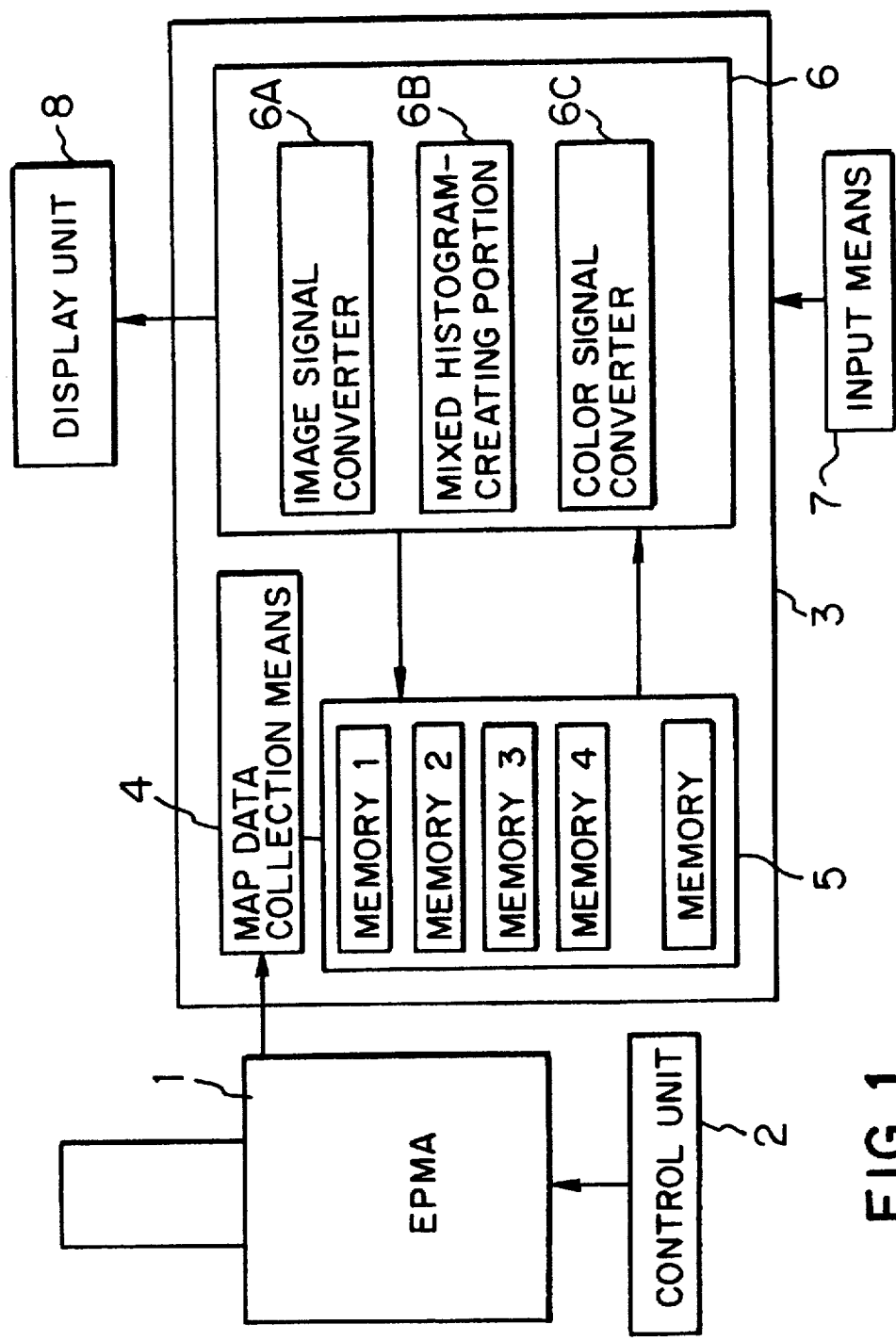
FIG. 1 is a schematic diagram of an electron probe microanalyzer according to the invention.

Referring to FIG. 1, an electron probe microanalyzer (EPMA) is schematically shown. This electron probe microanalyzer is one example of a surface analysis instrument according to the present invention. The body of the microanalyzer is indicated by numeral 1 and includes an electron gun, a focusing lens, a sample stage, an X-ray detector, and an optical microscope. These and other components of the body 1 of the microanalyzer is controlled by a control unit 2. Information obtained from the body 1 of the microanalyzer by making surface analyses is processed by a data processor 3. This data processor 3, for example, a programmed digital computer, comprises a map data collection means 4, an analyzed data memory 5, and a level assortment means 6. The map data collection means 4 stores the information obtained by the body 1 of the microanalyzer in the analyzed data memory 5. The level assortment means 6 reads information obtained by the surface analyses, i.e., data about the intensities of X-rays, from the memory 5 and assorts them according to their levels. An input means 7 is connected with the data processor 3. A display unit 8 is connected with the data processor 3.

The manner in which the electron probe microanalyzer constructed in this way operates when maps of intensities of characteristic X-rays emanating from different small regions are created and displayed is described below by referring to FIG. 2, which is a flowchart illustrating the operation.

Figure 3:
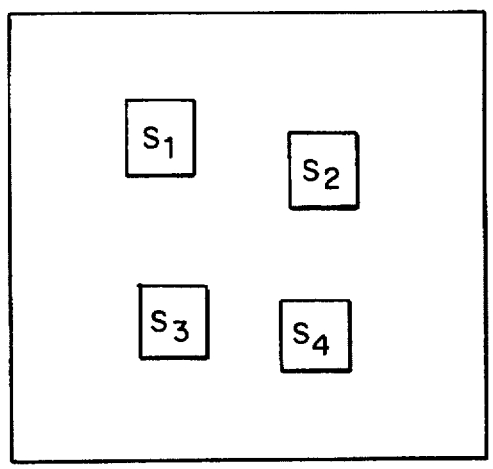
FIG. 3 is a diagram illustrating regions on a sample, the regions being analyzed by the electron probe microanalyzer shown in FIG. 1.

The body 1 of the electron probe microanalyzer incorporates the optical microscope to display an optical image of the sample on the display unit (not shown). A human operator designates regions to be analyzed through the use of the control unit 2 while monitoring the sample image (step 11). The operator also designates a chemical element to be investigated, also through the use of the control unit 2. For example, element A is designated (step 12). In FIG. 3, $S_1$, $S_2$, $S_3$, and $S_4$ show designated, analyzed small regions on the sample. Surface analyses are made in the order $S_1$, $S_2$, $S_3$, and $S_4$ (step 13). In these surface analyses, the height of the sample surface is adjusted optimally for each different small region.

The aforementioned information obtained from the small regions $S_1$, $S_2$, $S_3$, and $S_4$ is placed into areas 1, 2, 3, and 4 of the analyzed data memory 5 by the map data collection means 4 (step 14). The level assortment means 6 reads data about intensities of X-rays from the memory areas 1 to 4 and routes the data to an image signal converter 6A. For example, an instruction for displaying the map of characteristic X-ray intensities in 16 colors is entered. Then, the image signal converter 6A divides the dynamic range of accepted intensities of X-rays from the minimum value to the maximum value into 16 subranges. Different colors are assigned to these 16 subranges. When X-rays having an intensity lying in a subrange of intensities arrive, a color corresponding to the subrange is assigned to the X-rays. Signals indicating assigned colors are sent to the display unit 8. As a result, maps of the intensities of characteristic X-rays regarding the element A in the same regions $S_1$, $S_2$, $S_3$, and $S_4$ are displayed on the display unit 8 (step 15).

Then, the operator selects one from the maps 1 to 4 of the small regions $S_1$, $S_2$, $S_3$, and $S_4$ displayed on the display unit 8. Using the selected map, a level assortment is carried out. That is, colors are assigned to the intensities of the characteristic X-rays according to their levels (step 16). As an example, if the operator operates the input means 7 to specify the maps 1, 2, 3, and 4, then the level assortment means 6 reads data about the intensities of X-rays from the areas 1, 2, 3, and 4 of the analyzed data memory 5. The read data about the small regions $S_1$, $S_2$, $S_3$, and $S_4$ is sent to a mixed histogram-creating portion 6B incorporated in the level assortment means 6.

The mixed histogram-creating portion 6B first creates histograms as shown in FIGS. 4(a)–4(d) regarding the element A in the small regions $S_1$, $S_2$, $S_3$, and $S_4$, respectively. In each histogram, the intensities of characteristic X-rays are plotted on the horizontal axis while the number of analyzed points is plotted on the vertical axis. Then, the mixed histogram-creating portion 6B combines together these histograms into a mixed histogram, as shown in FIG. 4(e). The mixed histogram-creating portion 6B supplied an image signal representing this mixed histogram to the display unit 8. A window is displayed on the display unit 8, and the mixed histogram is displayed within this window (step 17). It is also possible to directly create the mixed histogram without creating the individual histograms of the small regions shown in FIGS. 4(a)–4(d).

Then, the operator assigns different colors to the intensities of characteristic X-rays arising from the element A according to the mixed histogram (step 18). For example, where the intensities are displayed in five colors, data exists in the intensity range of from 0 to 5000 within the mixed histogram. This range is divided into five equal subranges. Color $C_1$ is assigned to the intensity subrange of from 0 to 1000. Color $C_2$ is assigned to the intensity subrange of from 1000 to 2000. Color $C_3$ is assigned to the intensity subrange of from 2000 to 3000. Color $C_4$ is assigned to the intensity subrange of from 3000 to 4000. Color $C_5$ is assigned to the intensity subrange of from 4000 to 5000. The operator may determine this assignment of the colors through the input means 7. Alternatively, the assignment may be automatically done by previously determining the order in which the colors are assigned. Information indicating the results of the assortment of the levels, i.e., information indicating the relation of the subranges of the X-ray intensities to the colors, is sent to a color signal converter 6C included in the level assortment means 6 and stored there.

Figure 5:
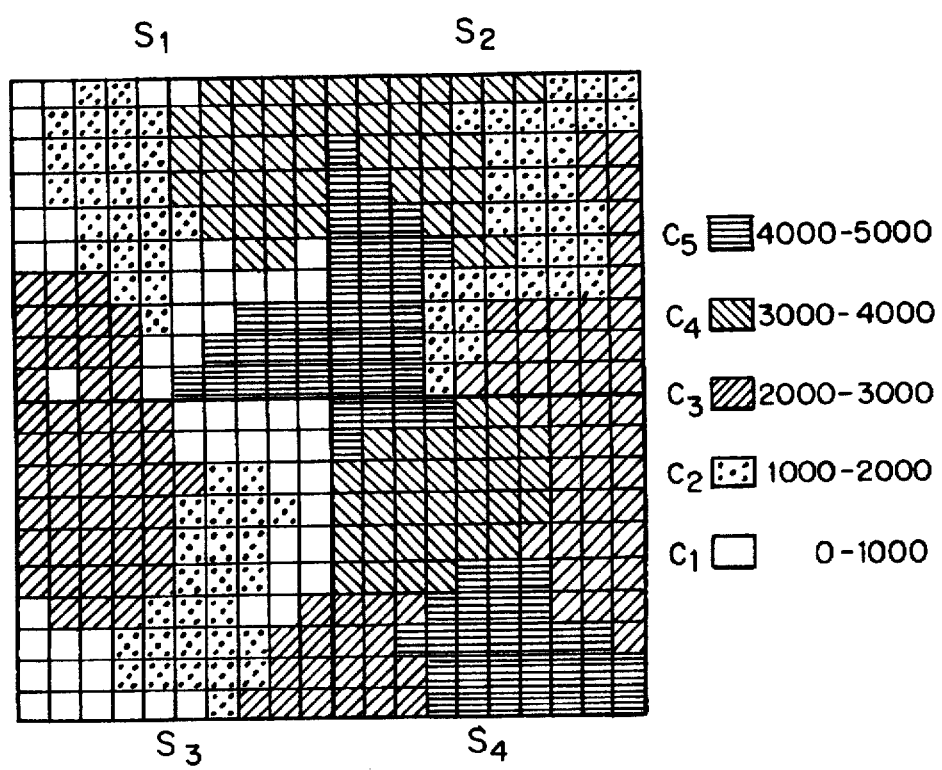
FIG. 5 is a characteristic X-ray intensity map displayed on the display unit of the electron probe microanalyzer shown in FIG. 1.

After this level assortment, the level assortment means 6 reads data about X-ray intensities from the areas 1, 2, 3, and 4 of the analyzed data memory 5 and sends data about the intensities of X-rays originating from the small regions $S_1$, $S_2$, $S_3$, and $S_4$ to the color signal converter 6C. The colors $C_1$–$C_5$ are selected according to the intensities of the X-rays. The color signal converter 6C converts information indicating the results of the level assortment stored in the converter into color signals and sends these color signals to the display unit 8 (step 19). As a result, maps of the intensities of the characteristic X-rays emanating from the element A in the small regions $S_1$, $S_2$, $S_3$, and $S_4$ are displayed on the display unit 8 as shown in FIG. 5. In these maps, the colors are assigned to the intensities according to the common level assortment.

In the electron probe microanalyzer shown in FIG. 1, only one level assortment operation is necessary because the mixed histogram is created. It is easy to compare the maps with each other.

In the electron probe microanalyzer shown in FIG. 1, maps of weighted concentrations in the regions $S_1$, $S_2$, $S_3$, and $S_4$ can be displayed on the display unit by converting the X-ray intensities stored in the analyzed data memory 5 into weighted concentrations, creating a histogram of the weighted concentrations by means of the mixed histogram-creating portion 6B and performing other processing described above.

In the above description, maps 1, 2, 3, and 4 are selected to assort the levels. Any desired map can be selected. Where only one map is selected, creation of the mixed histogram can be omitted.

Figure 6:
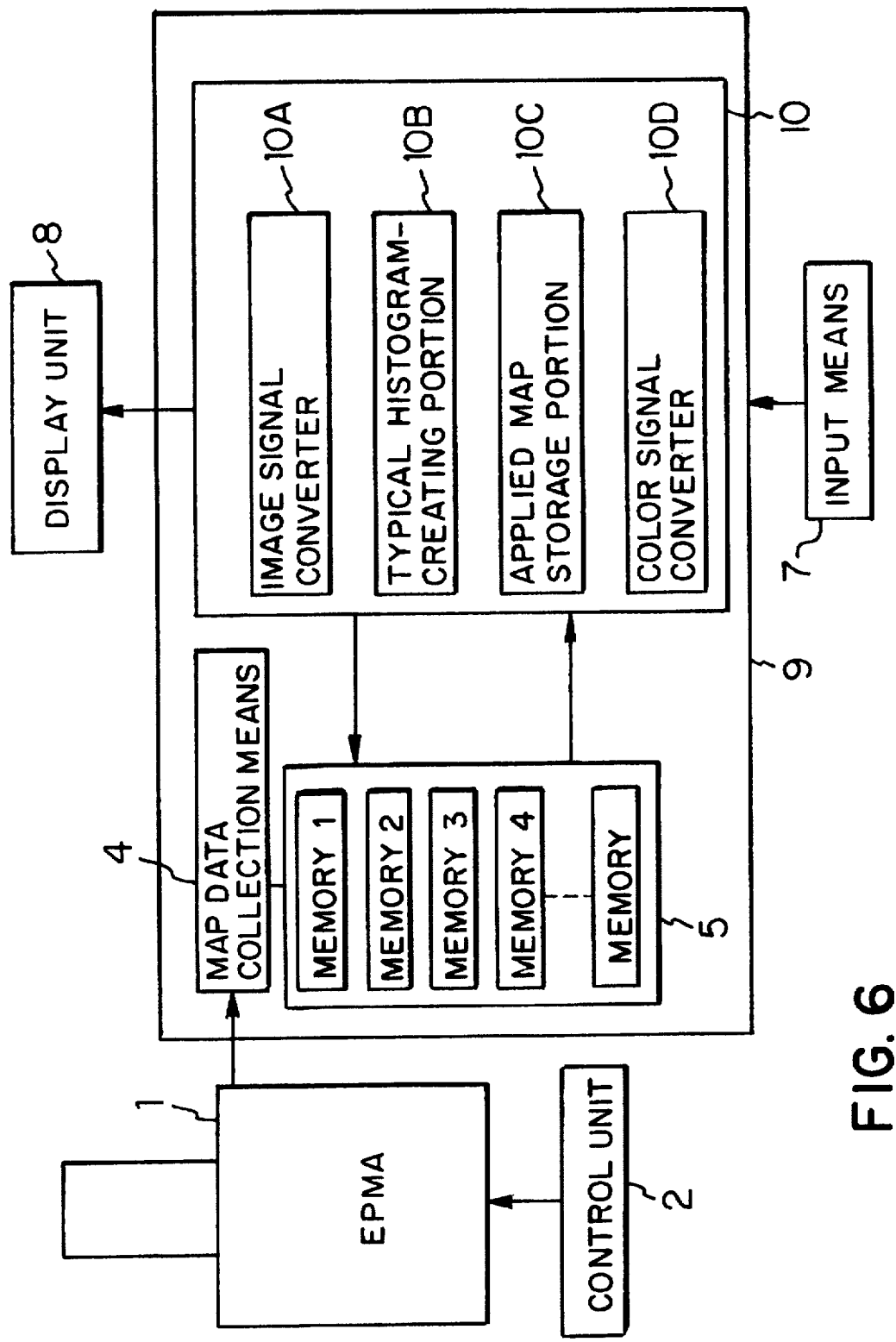
FIG. 6 is a schematic diagram of another electron probe microanalyzer according to the invention.

Referring next to FIG. 6, there is shown another electron probe microanalyzer (one example of surface analysis instrument) according to the present invention. It is to be noted that like components are indicated by like reference numerals in various figures and that those components which have been already described will not be described below. A data processor 9 processes data obtained from the body 1 of the electron probe microanalyzer (EPMA) which performs surface analyses. The data processor 9 is equipped with a map data collection means 4, an analyzed data memory 5, and a level assortment means 10. The level assortment means 10 reads data about the intensities of X-rays obtained by performing surface analyses from the analyzed data memory 5 and performs a level assortment.

Figure 7:
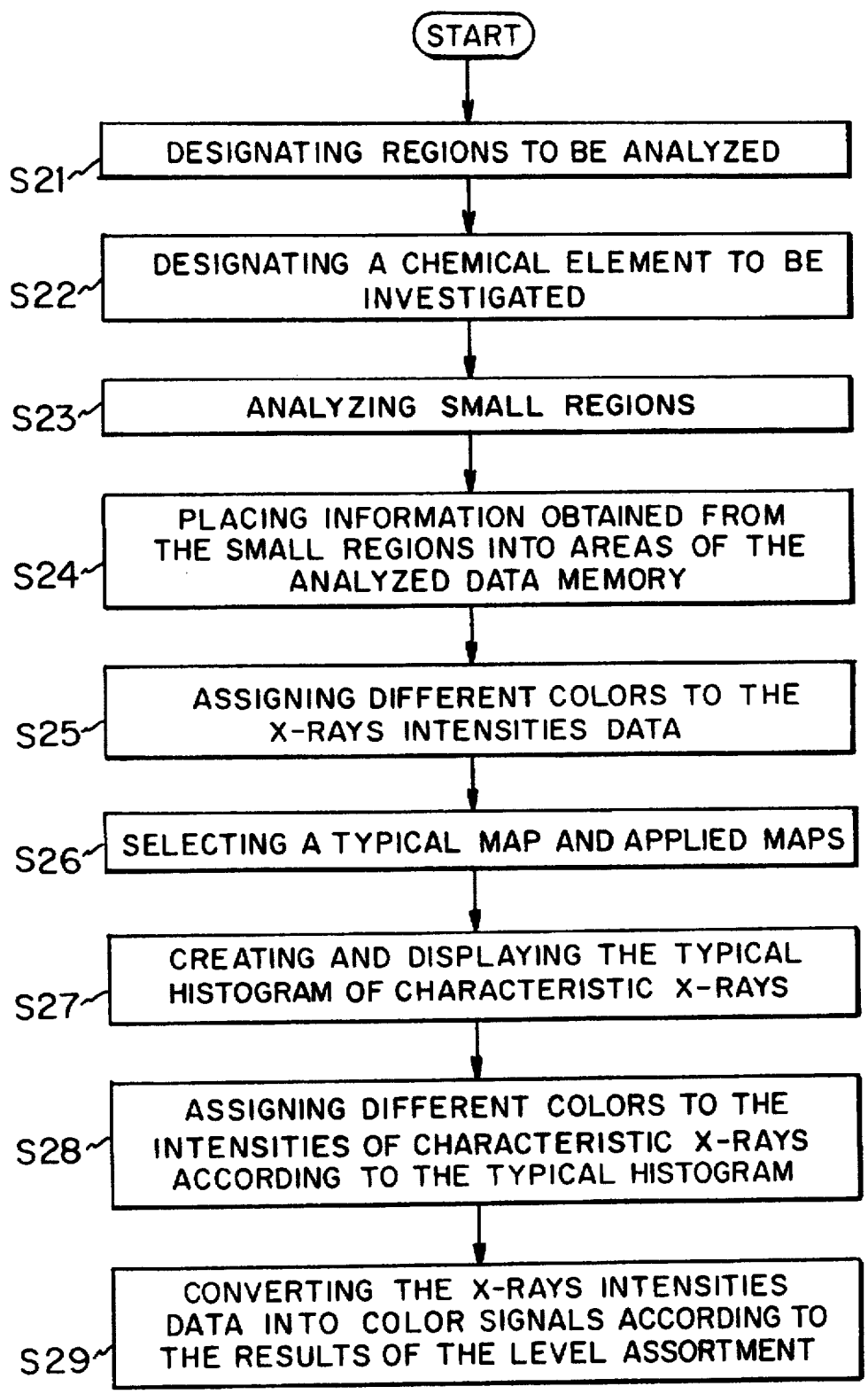
FIG. 7 is a diagram illustrating the operation of the electron probe microanalyzer shown in FIG. 6.

The manner in which the instrument constructed in this way operates when maps of intensities of characteristic X-rays emanating from plural small regions are displayed is described below by referring to the flowchart of FIG. 7.

Figure 2:
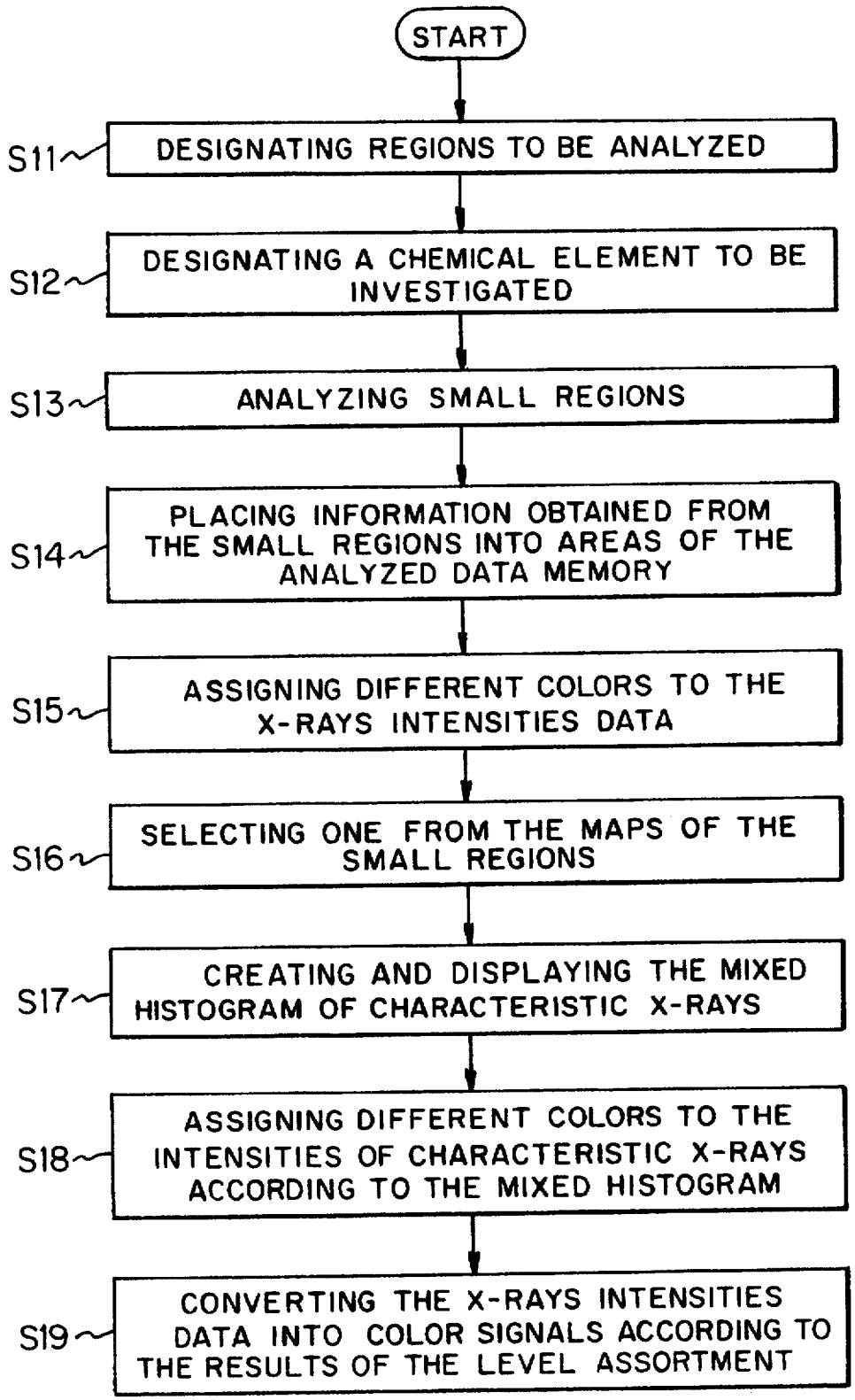
FIG. 2 is a diagram illustrating the operation of the electron probe microanalyzer shown in FIG. 1.

The steps beginning with the designation of analyzed regions (step 21) and ending with the display of the maps of characteristic X-rays emitted from the analyzed regions (step 25) are the same as those of the process illustrated in the flowchart of FIG. 2.

In step 26, the operator selects a typical map, where a level assortment is made, from maps 1 to 4 of the small regions $S_1$, $S_2$, $S_3$, and $S_4$ presented on the display unit 8, and selects a map to which the level assortment is to be applied. For example, if the map 1 is selected as the typical map through the input means 7, then the level assortment means 10 reads data about the intensities of X-rays from the area 1 of the analyzed data memory 5. The data is then sent to a typical histogram-creating portion 10B included in the level assortment means 10. If the maps 1, 2, 3, and 4 are selected as applied maps through the input means 7, then the results of the selection are sent to an applied map storage portion 10C included in the level assortment means 10.

Figure 4A:
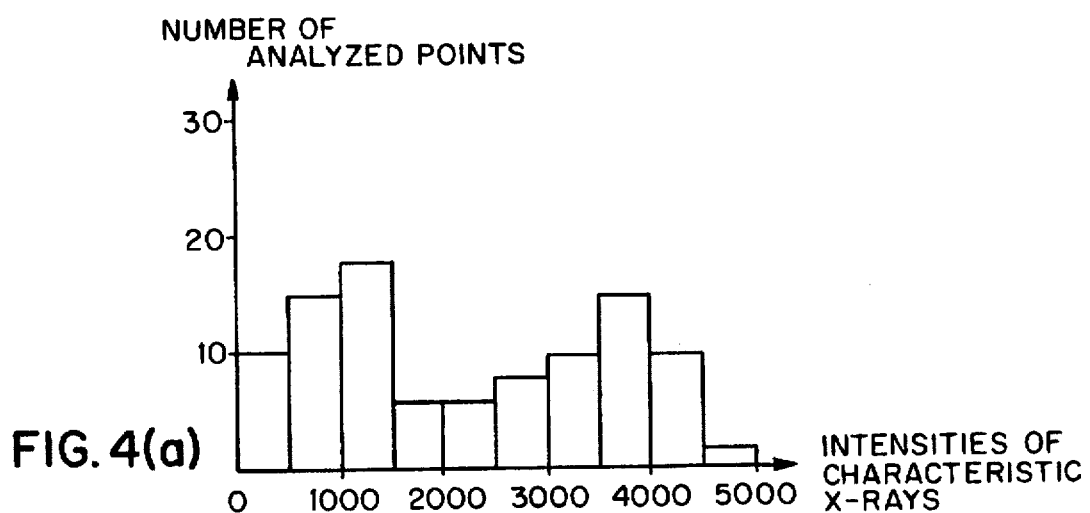
FIGS. 4(a)–4(e) are histograms illustrating the operation of the electron probe microanalyzer shown in FIG. 1.
Figure 4B:
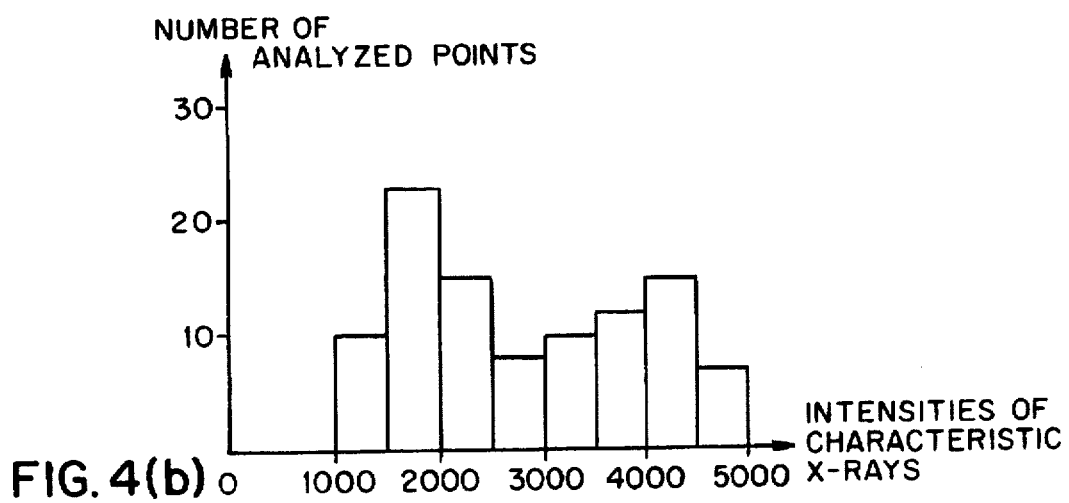
Figure 4C:
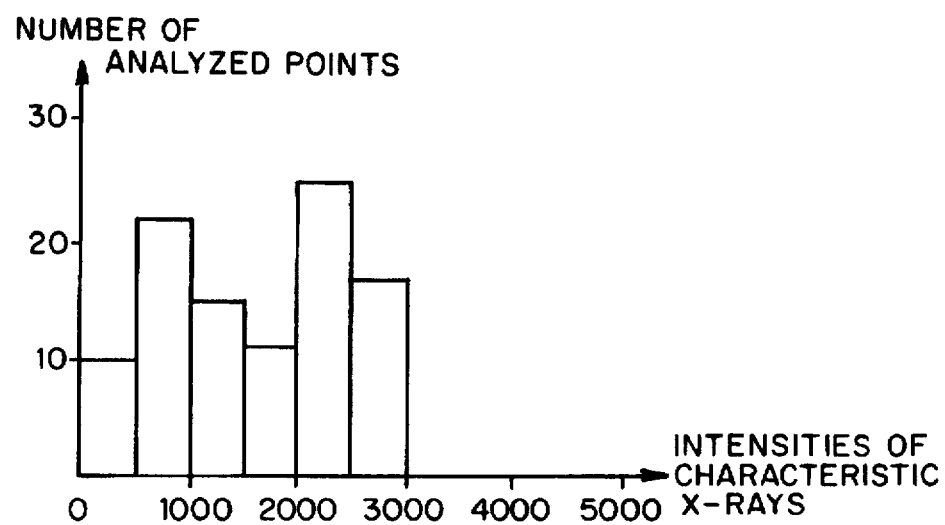
Figure 4D:
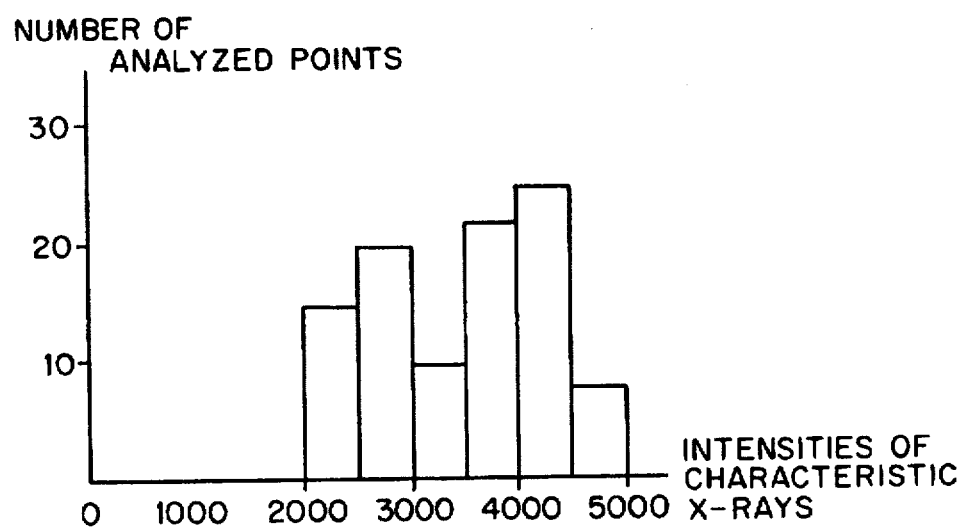
Figure 4E:
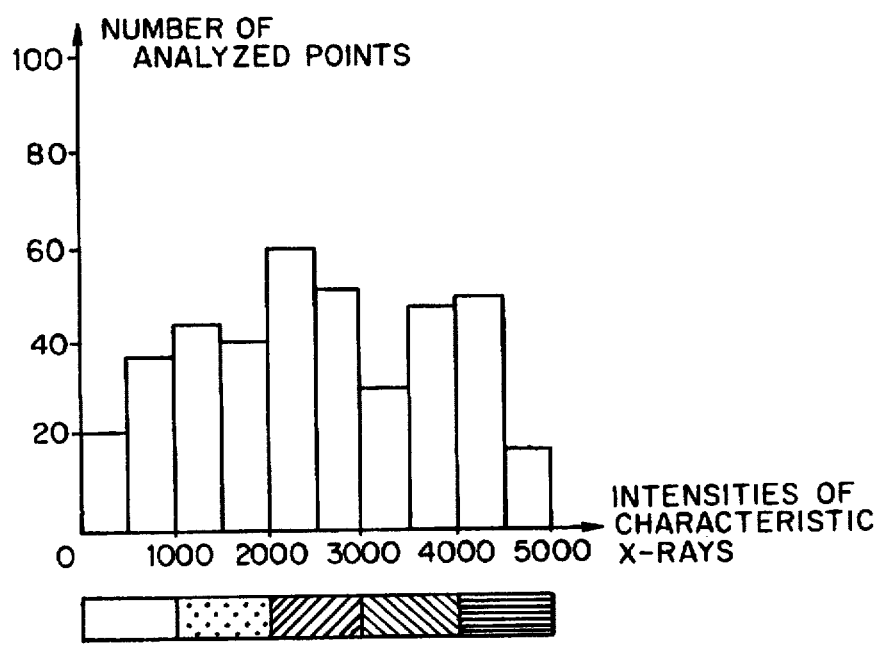

The typical histogram-creating portion 10B creates a histogram of the element A in the small region $S_1$, as shown in FIG. 4(a), according to the data read from the area 1 of the memory 5, i.e., data about the intensities of the X-rays produced from the region $S_1$. The typical histogram-creating portion 10B supplies an image signal indicating this typical histogram to the display unit 8. As a result, this typical histogram is displayed within a window presented on the viewing screen of the display unit 8 (step 27).

Then, the operator assigns different colors to the intensities of characteristic X-rays arising from the element A according to this typical histogram (step 28). For example, where the intensities are displayed in five colors, data exists in the intensity range of from 1 to 5000 within the typical histogram. This range is divided into five equal subranges. Color $C_1$ is assigned to characteristic X-rays having intensities lying in the subrange of from 0 to 1000. Color $C_2$ is assigned to characteristic X-rays having intensities lying in the subrange of from 1000 to 2000. Color $C_3$ is assigned to characteristic X-rays having intensities lying in the subrange of from 2000 to 3000. Color $C_4$ is assigned to characteristic X-rays having intensities lying in the subrange of from 3000 to 4000. Color $C_5$ is assigned to characteristic X-rays having intensities lying in the subrange of from 4000 to 5000. This color assignment may be carried out either manually by the operator through the input means 7 or automatically. Information indicating the results of the level assortment is sent to a color signal converter 10D included in the level assortment means 10.

After this level assortment, the level assortment means 10 reads data about the intensities of the X-rays concerning the applied maps 1, 2, 3, and 4 from the areas 1, 2, 3, and 4 of the memory. The read data about the small regions $S_1$, $S_2$, $S_3$, and $S_4$ is sent to the color signal converter 10D. This converter 10D converts the intensities of the X-rays into color signals for displaying the intensities in the colors $C_1$–$C_5$ according to the results of the aforementioned level assortment and sends the color signals to the display unit 8 (step 29). As a result, maps of the intensities of the characteristic X-rays emanating from the element A in the small regions $S_1$, $S_2$, $S_3$, and $S_4$ are shown, as pictured in FIG. 5. In these maps, the intensities are displayed in the colors $C_1$–$C_5$.

In the electron probe microanalyzer shown in FIG. 6, a typical histogram is created from data obtained by making surface analyses of the specified regions. The level assortment is carried out. This level assortment is also applied to the data about the intensities of X-rays from other regions, and then maps are created. Hence, the maps can be compared easily.

In the electron probe microanalyzer shown in FIG. 6, maps of weighted concentrations in the regions $S_1$, $S_2$, $S_3$, and $S_4$ can be displayed on the display unit by converting the X-ray intensities stored in the analyzed data memory 5 into weighted concentrations, creating a typical histogram of the weighted concentrations by means of the typical histogram-creating portion 10B, and performing other processing described above.

In the above description, map 1 is selected as a typical map used for level assortment, and maps 1, 2, 3, and 4 are selected as applied maps. These maps can be selected at will.

In the electron probe microanalyzer shown in FIG. 6, selection of the typical map and applied maps is carried out in one step (step 26). The selection of the applied maps may be carried out subsequently to the level assortment (step 28).

In the above descriptions, maps of regions not adjacent to each other are displayed. The present invention can also be applied to the case in which maps of adjacent small regions are connected to each other and displayed.

It is to be understood that the present invention is not limited to the above examples and that various changes and modifications are possible. In the above examples, the invention is applied to surface analysis performed using an EPMA. Obviously, the invention can also be applied to other surface analysis instruments consisting of an X-ray analysis instrument such as an X-ray fluorescence spectrometer.

As can be understood from the description provided thus far according to the present invention, levels are assorted using a mixed histogram or a selected typical histogram. The level assortment is applied to every map and the levels are displayed. Therefore, the level assortment can be done efficiently. It is easy to compare the maps with each other.

Having thus described our invention with the detail and particularity required by the Patent Laws, what is desired protected by Letters Patent is set forth in the following claims.

What is claimed is:

1. A surface analysis instrument comprising:

a means for making surface analyses of different regions on a sample to obtain information about said regions in the format of a two dimension distribution of intensity data for each region;

a means for creating a mixed histogram of said intensity data for said regions from said information obtained by said surface analyses;

a means for determining the dynamic range of the mixed histogram and based thereon performing an assortment by intensity level from said mixed histogram;

a storage means in which information about said intensity level assortment is stored;

an assorting means for assorting images of said regions according to said intensity levels based on said information about said intensity level assortment; and a display means having a viewing screen on which said images of said different regions are displayed at different positions.

2. The surface analysis instrument of claim 1, wherein said surface analysis instrument is an electron probe microanalyzer.

3. The surface analysis instrument of claim 1, wherein said assorting means assigns colors to said images of said regions according to said information about said intensity level assortment to display said images in the colors.

4. A surface analysis instrument comprising:

a means for making surface analyses of different regions on a sample to obtain information about said regions in the format of a two dimension distribution of intensity data for each region;

a means for permitting a user to select one from said regions;

a means for creating a histogram of said intensity data for said selected region from information about this region;

a means for determining the dynamic range of said histogram and based thereon performing an intensity level assortment according to said histogram;

an assorting means for assorting images of said regions according to said intensity levels, based on said information about said intensity level assortment; and a display means having a viewing screen on which said images of said different regions are displayed at different positions.

5. The surface analysis instrument of claim 4, wherein said surface analysis instrument is an electron probe microanalyzer.

6. The surface analysis instrument of claim 4, wherein said assorting means assigns colors to said images of said regions according to said information about said intensity level assortment to display said images in the colors.

7. A method of displaying images, using information obtained by performing surface analyses, said method comprising the steps:

making surface analyses of different regions on a sample in the format of a two dimension distribution of intensity data for each region;

creating a mixed histogram of said intensity data for said different regions from information obtained by said surface analyses;

determining the dynamic range of said mixed histogram and based thereon performing an intensity level assortment according to said mixed histogram; and displaying images of said different regions according to results of said intensity level assortment at different positions on a viewing screen.

8. A method of displaying images, using information obtained by performing surface analyses as set forth in claim 7, wherein said surface analyses are made by an electron probe microanalyzer.

9. A method of displaying images, using information obtained by performing surface analyses as set forth in claim 7, wherein said step for performing a level assortment further comprises assigning colors to said images of said regions according to information about said level assortment to display said images in the colors.

10. A method of displaying images, using information obtained by performing surface analyses, said method comprising the steps:

making surface analyses of different regions on a sample to obtain information about said regions in the format of a two dimension distribution of intensity data for each region;

selecting one from said regions;

creating a histogram of said intensity data for said selected region from information about this selected region;

determining the dynamic range of said histogram and based thereon performing an intensity level assortment according to said histogram; and applying results of said intensity level assortment to information about said different regions to display images of said different regions at different positions on a viewing screen.

11. A method of displaying images, using information obtained by performing surface analyses as set forth in claim 10, wherein said surface analyses are made by an electron probe microanalyzer.

12. A method of displaying images, using information obtained by performing surface analyses as set forth in claim 10, wherein colors are assigned to said images of said regions according to information about said level assignment and said images are displayed in the colors.

* * * * *